United States Patent
Benke

(10) Patent No.: US 8,586,082 B2
(45) Date of Patent: Nov. 19, 2013

(54) SOLID ORALLY ADMINISTERABLE PHARMACEUTICAL DOSAGE FORMS WITH RAPID ACTIVE PRINCIPLE RELEASE

(75) Inventor: Klaus Benke, Bergisch Gladbach (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 1284 days.

(21) Appl. No.: 12/089,148

(22) PCT Filed: Sep. 21, 2006

(86) PCT No.: PCT/EP2006/009178
§ 371 (c)(1),
(2), (4) Date: Jul. 2, 2008

(87) PCT Pub. No.: WO2007/039122
PCT Pub. Date: Apr. 12, 2007

(65) Prior Publication Data
US 2010/0151011 A1    Jun. 17, 2010

(30) Foreign Application Priority Data
Oct. 4, 2005 (DE) .......................... 10 2005 047 561

(51) Int. Cl.
*A61K 9/58* (2006.01)
*A61K 9/00* (2006.01)
*A61K 9/20* (2006.01)
*A61K 31/5375* (2006.01)
*C07D 413/00* (2006.01)

(52) U.S. Cl.
USPC ......... 424/452; 424/400; 424/465; 514/236.8

(58) Field of Classification Search
USPC ......... 424/452, 400, 465; 514/236.8; 544/137
See application file for complete search history.

(56) References Cited

U.S. PATENT DOCUMENTS

| | | |
|---|---|---|
| 2,811,555 A | 10/1957 | Larive et al. |
| 3,279,880 A | 10/1966 | Straley et al. |
| 4,128,654 A | 12/1978 | Fugitt et al. |
| 4,250,318 A | 2/1981 | Dostert et al. |
| 4,327,725 A | 5/1982 | Cortese et al. |
| 4,344,934 A | 8/1982 | Martin et al. |
| 4,500,519 A | 2/1985 | Lormeau et al. |
| 4,705,779 A | 11/1987 | Madi-Szabo et al. |
| 4,765,989 A | 8/1988 | Wong et al. |
| 4,948,801 A | 8/1990 | Carlson et al. |
| 4,977,173 A | 12/1990 | Brittelli et al. |
| 5,002,937 A | 3/1991 | Bosies et al. |
| 5,254,577 A | 10/1993 | Carlson et al. |
| 5,349,045 A | 9/1994 | Jiang |
| 5,532,255 A | 7/1996 | Raddatz et al. |
| 5,561,148 A | 10/1996 | Gante et al. |
| 5,564,571 A | 10/1996 | Barbachyn et al. |
| 5,654,428 A | 8/1997 | Barbachyn et al. |
| 5,654,435 A | 8/1997 | Barbachyn et al. |
| 5,688,792 A | 11/1997 | Barbachyn et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,827,857 A | 10/1998 | Riedl et al. |
| 5,910,504 A | 6/1999 | Hutchinson et al. |
| 5,922,708 A | 7/1999 | Riedl et al. |
| 5,928,660 A * | 7/1999 | Kobayashi et al. ........... 424/401 |
| 5,929,248 A | 7/1999 | Barbachyn et al. |
| 5,935,724 A | 8/1999 | Spillman et al. |
| 5,972,947 A | 10/1999 | Tsaklakidis et al. |
| 5,977,373 A | 11/1999 | Gadwood et al. |
| 5,998,406 A | 12/1999 | Hester et al. |
| 6,069,160 A | 5/2000 | Stolle et al. |
| 6,074,670 A | 6/2000 | Stamm et al. |
| 6,218,413 B1 | 4/2001 | Hester et al. |
| 6,239,152 B1 | 5/2001 | Gordeev et al. |
| 6,251,869 B1 | 6/2001 | Bohanon |
| 6,265,178 B1 | 7/2001 | Martin, Jr. |
| 6,281,210 B1 | 8/2001 | Hester, Jr. |
| 6,294,201 B1 | 9/2001 | Kettelhoit et al. |
| 6,413,981 B1 | 7/2002 | Paget et al. |
| 6,458,793 B1 | 10/2002 | Warner et al. |
| 6,514,529 B2 | 2/2003 | Yamamoto et al. |
| 6,805,881 B1 | 10/2004 | Kanikanti et al. |

(Continued)

FOREIGN PATENT DOCUMENTS

| | | |
|---|---|---|
| AU | 744002 B2 | 7/1999 |
| DE | 2836305 A1 | 3/1979 |

(Continued)

OTHER PUBLICATIONS

Breitenbach ("Melt extrusion: from process to drug delivery technology," in European Journal of Pharmaceutics and Biopharmaceutics 54 (2002) 107-117).*
Chiou, W.L. et al. Pharmaceutical Applications of Solid Dispersion Systems. Journal of Pharmaceutical Sciences 60, (1971). 128-1302.
Ford, J.L. The Current Status of Solid Dispersions. Pharm Acta Helv. 61, (1986)69-88.
Rasenack, N. et al. Poorly Water-soluble Drugs for Oral Delivery- A Challenge for Pharmaceutical Development. Pharmazeutische Industrie 67, Nr. 5 (2005), 583-591.
Breitenbach, J. Melt extrusion: from process to drug delivery technology. European Journal of Pharmaceutics and Biopharmaceutics 54 (2002) 107-117.

(Continued)

*Primary Examiner* — Blessing Fubara
(74) *Attorney, Agent, or Firm* — Buchanan Ingersoll & Rooney PC

(57) ABSTRACT

The present invention relates to solid pharmaceutical dosage forms which can be administered orally and comprise 5-chloro-N-({(5S)-2-oxo-3-[4-(3-oxo-4-morpholinyl)phenyl]-1,3-oxazolidin-5-yl}methyl)-2-thiophenecarboxamide in amorphous form and/or thermodynamically metastable crystal modification and have rapid release of active ingredient, and to process for the production thereof, the use thereof as medicament, the use thereof for the prophylaxis, secondary prophylaxis and/or treatment of disorders, and to the use thereof for producing a medicament for the prophylaxis, secondary prophylaxis and/or treatment of disorders.

25 Claims, No Drawings

(56) References Cited

U.S. PATENT DOCUMENTS

| | | | |
|---|---|---|---|
| 6,818,243 | B2 | 11/2004 | Nagashima et al. |
| 7,034,017 | B2 | 4/2006 | Straub et al. |
| 7,078,417 | B2 | 7/2006 | Rosentreter et al. |
| 7,109,218 | B2 | 9/2006 | Rosentreter et al. |
| 7,129,255 | B2 | 10/2006 | Rosentreter et al. |
| 7,157,456 | B2 | 1/2007 | Straub et al. |
| 7,351,823 | B2 | 4/2008 | Berwe et al. |
| 2001/0029351 | A1 | 10/2001 | Falotico et al. |
| 2001/0046987 | A1 | 11/2001 | Hester et al. |
| 2003/0153610 | A1* | 8/2003 | Straub et al. .................. 514/376 |
| 2003/0161882 | A1 | 8/2003 | Waterman |
| 2004/0102450 | A1 | 5/2004 | Ewing et al. |
| 2004/0162427 | A1 | 8/2004 | Rosentreter et al. |
| 2004/0242660 | A1 | 12/2004 | Straub et al. |
| 2005/0064006 | A1 | 3/2005 | Perzborn et al. |
| 2005/0182055 | A1 | 8/2005 | Berwe et al. |
| 2005/0261502 | A1 | 11/2005 | Rosentreter et al. |
| 2006/0154969 | A1 | 7/2006 | Rosentreter et al. |
| 2006/0258724 | A1 | 11/2006 | Straub et al. |
| 2007/0026065 | A1 | 2/2007 | Benke et al. |
| 2007/0149522 | A1 | 6/2007 | Thomas |
| 2008/0026057 | A1 | 1/2008 | Benke |

FOREIGN PATENT DOCUMENTS

| | | | |
|---|---|---|---|
| DE | 3417113 | A1 | 11/1984 |
| DE | 196 04 223 | A1 | 8/1997 |
| DE | 19962924 | A1 | 7/2001 |
| DE | 10355461 | A1 | 6/2005 |
| EP | 0 127 902 | A2 | 12/1984 |
| EP | 0 316 594 | A1 | 5/1989 |
| EP | 0 352 781 | A2 | 1/1990 |
| EP | 0350002 | A1 | 1/1990 |
| EP | 0 623 615 | A1 | 11/1994 |
| EP | 0645376 | A1 | 3/1995 |
| EP | 0 738 726 | A1 | 10/1996 |
| EP | 0 785 200 | A2 | 7/1997 |
| EP | 0930076 | A1 | 7/1999 |
| EP | 0950386 | A2 | 10/1999 |
| EP | 1024793 | A1 | 8/2000 |
| EP | 1113787 | A1 | 7/2001 |
| GB | 2140687 | | 11/1984 |
| GB | 2140687 | | 12/1984 |
| WO | WO-93/09103 | A1 | 5/1993 |
| WO | WO-93/23384 | A1 | 11/1993 |
| WO | WO-97/03072 | A1 | 1/1997 |
| WO | WO-97/09328 | A1 | 3/1997 |
| WO | WO-97/10223 | A1 | 3/1997 |
| WO | WO-98/01446 | A1 | 1/1998 |
| WO | WO-98/54161 | A1 | 12/1998 |
| WO | WO-99/02525 | A1 | 1/1999 |
| WO | WO-99/03846 | A1 | 1/1999 |
| WO | WO-99/06371 | A1 | 2/1999 |
| WO | WO-99/21535 | | 5/1999 |
| WO | WO-99/21535 | A1 | 5/1999 |
| WO | WO-99/24428 | A1 | 5/1999 |
| WO | WO-99/29688 | A1 | 6/1999 |
| WO | WO-99/31092 | A1 | 6/1999 |
| WO | WO-99/37304 | A1 | 7/1999 |
| WO | WO-99/37630 | A1 | 7/1999 |
| WO | WO-99/37641 | A1 | 7/1999 |
| WO | WO-99/40094 | A1 | 8/1999 |
| WO | WO-99/59616 | A1 | 11/1999 |
| WO | WO-00/16748 | | 3/2000 |
| WO | WO-00/16748 | A1 | 3/2000 |
| WO | WO-01/42242 | A1 | 6/2001 |
| WO | WO-01/44212 | A1 | 6/2001 |
| WO | WO-01/46185 | A1 | 6/2001 |
| WO | 01/47919 | | 7/2001 |
| WO | WO-01/47949 | A1 | 7/2001 |
| WO | WO-02/15940 | A2 | 2/2002 |
| WO | WO-02/25210 | A1 | 3/2002 |
| WO | WO-02/38126 | A2 | 5/2002 |
| WO | WO-02/064575 | A1 | 8/2002 |
| WO | WO-02/070484 | A1 | 9/2002 |
| WO | WO-02/070485 | A1 | 9/2002 |
| WO | WO-02/070520 | A1 | 9/2002 |
| WO | WO-02/079195 | A1 | 10/2002 |
| WO | WO-02/079196 | A1 | 10/2002 |
| WO | WO-03/000256 | A1 | 1/2003 |
| WO | WO-03/008384 | A1 | 1/2003 |
| WO | WO-03/035133 | A1 | 5/2003 |
| WO | WO-03/053441 | A1 | 7/2003 |
| WO | WO-2004/066910 | A2 | 8/2004 |
| WO | 2005/060940 | A1 | 7/2005 |
| WO | WO-2005/068456 | A1 | 7/2005 |
| WO | 2006/072367 | A1 | 7/2006 |
| WO | WO-2006/079474 | A1 | 8/2006 |
| WO | WO-2007/036306 | A1 | 4/2007 |
| WO | WO-2007/039122 | A2 | 4/2007 |
| WO | WO-2007/039132 | A1 | 4/2007 |
| WO | WO-2007/039134 | A1 | 4/2007 |
| WO | WO-2007/042146 | A1 | 4/2007 |
| WO | WO-2008/012002 | A1 | 1/2008 |
| WO | WO-2008/052671 | A1 | 5/2008 |

OTHER PUBLICATIONS

Breitenbach, J. Feste Loesungen durch Sclimelzextrusion—ein integriertes Herstellkonzept. Pharmazie in unserer Zeit 29 (2000), 46-49.

"About FDA: The Biopharmaceutics Classification System (BCS) Guidance" of the US Food and Drug Administration, Jun. 3, 2009.

"British Pharmacopoeia 2009," vol. I & II, General Notices Part II: Solubility.

Advisory Action mailed Jan. 25, 2011, in U.S. Appl. No. 11/317,720.

Alderman, "A Review of Cellulose Ethers in Hydrophilic Materices for Oral Controlled-Release Dosage Forms", Int. J. Pharm. Tech. & Prod. Mfr., 1984, vol. 5, No. 3, pp. 1-9.

Amendment mailed Jul. 28, 2010, in U.S. Appl. No. 11/317,720.

Amendment mailed Nov. 1, 2010, in U.S. Appl. No. 10/580,711.

Aulton, "Pharmaceutics: The Science of Dosage Form Design", 1998, pp. 136-137 and 154-156.

Breitenbach, "Feste Loesungen durch Schmelzextrusion- ein integriertes Herstellkonzept", Pharmazie in unserver Zeit, 2000, Nr.1, pp. 46-50.

Breitenbach, "Melt Extrusion: From Process to Drug Delivery Technology", European Journal of Pharmaceutics and Biopharmaceutics, 2002, vol. 54, pp. 107-117.

Communication dated Mar. 31, 2010 in Opposition to EP 1 689 370B1.

Datasheet for Zyvoxid from South African Electronic Package Inserts, May 29, 2001.

European Patent Office Communication of a Notice of Opposition dated Nov. 20, 2008 for EP 1689370 B1.

Final Office Action mailed Jan. 19, 2011, in U.S. Appl. No. 10/580,711.

Gandhi et al., "Extrusion and Spheronization in the Development of Oral Controlled-Release Dosage Forms", PSTT, 1999, vol. 2, No. 4, pp. 160.

Hilgers, et al., "Predicting Oral Absorption of Drugs: a case . . . ," 2003, Pharmaceutical Research, 20(8), pp. 1149-1155.

Kubitza et al., "Safety, Pharmacodynamics, and Pharmacokinetics of a Single Doses of BAY 59/7939, an Oral, Direct Factor Xa Inhibitor", Pharmacodynamics and Drug Action, 2005.

Lippold, "Controlled Release Products: Approaches of Pharmaceutical Technology," Oral Controlled Release Products: Therapeutic and Biopharmaceutic Assessment, editors U. Gundert-Remy and H. Moeller, 1989, pp. 39-57, Stuttgart, Germany.

Melia, "Hydrophilic Matrix Sustained Release Systems Based on Polysaccharide Carriers", Critical Reviews in Therapeutic Drug Carrier Systems, 1991, vol. 8, No. 4, pp. 395-421.

Muller, et al., "Emulsion and Nanosuspensions for the Formulation of Poorly Soluble Drugs," 1997, pp. 20.

Office Action mailed Apr. 15, 2010, in U.S. Appl. No. 11/317,720.

Office Action mailed Aug. 18, 2010, in U.S. Appl. No. 10/580,711.

Office Action mailed Oct. 13, 2010, in U.S. Appl. No. 11/317,720.

Opposition of Ratiopharm GmbH to EP Patent 1 830 855 B1 filed Nov. 23, 2010.

(56) References Cited

OTHER PUBLICATIONS

Opposition of Sandoz GmbH to EP Patent 1 830 855 B1 filed Nov. 24, 2010.
Opposition to EP 1689370 B1 filed Nov. 12, 2008 by ratiopharm GmbH.
Pfizer, "Gebrauchsinformation: Information Fuer Den Anwender," Stand der Informationen: Oct. 2008.
Pfizer, "Zyvoxid® Linezolid," Prescribing Information in Israel, Apr. 20, 2006.
Preliminary Amendment in RCE filed Mar. 14, 2011, in U.S. Appl. No. 11/317,720.
Reply to Patentee's Statement dated Jun. 15, 2009, filed in European Patent Office on Jan. 8, 2010.
Reply to the Opposition to EP Patent 1689370 filed Jun. 15, 2009.
Response to Final Office Action mailed Jan. 13, 2011, in U.S. Appl. No. 11/317,720.
Santus et al., "Osmotic Drug Delivery: A Review of the Patent Literature", Journal of Controlled Release, 1995, vol. 35, pp. 1-21.
Vazquez et al., "Influence of Technological Variables on Release of Drugs From Hydrophilic Matrices", Drug Development and Industrial Pharmacy, 1992, vol. 18 No. 11&12, pp. 1355-1375.
Verma et al., "Formulation Aspects in the Development of Osmotically Controlled Oral Drug Delivery Systems", Journal of Controlled Release, 2002, vol. 79, pp. 7-27.
Verma et al., "Osmotically Controlled Oral Drug Delivery", Drug Deveopment and Industrial Pharmacy, 2000, vol. 26, No. 7, pp. 695-708.
Verma, et al., "Osmotically controlled oral drug delivery," 2000, Drug Development and Industrial Pharmacy 26(7), pp. 695-708.
Provisional Opinion of the European Opposition Divisional in Opposition to EP Application 04797879, dated Jan. 14, 2011 (10 pages).
Weinz et al., "In vitro metabolism of BAY 59/7939—an oral, direct Factor Xa inhibitor", Drug Drug Metabolism Reviews, 2004, vol. 36, No. Suppl. 1, pp. 98.
Bono, F., et al., "Human Umbilical Vein Endothelial Cells Express High Affinity Receptors for Factor Xa", Journal of Cellular Physiology, 1997, vol. 172, pp. 36-43.
Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.
Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.
Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.
Altieri, D. C., et al., "Identification of Effector Cell Protease Receptor-1", The Journal of Immunology, 1990, vol. 145, No. 1, pp. 246-253.
Coughlin, S. R., "Thrombin Signalling and Protease-Activated Receptors", Nature, 2000, vol. 407, pp. 258-264.
Ornstein, D. L., et al., "Cancer, Thrombosis, and Anticoagulants", Current Opinion in Pulmonary Medicine, 2000, vol. 6, pp. 301-308.
Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409,.
Herault, J-P., et al., "Activation of Human Vascular Endothelial Cells by Factor Xa: Effect of Specific Inhibitors", Biochemical Pharmacology, 1999, vol. 57, pp. 603-610.
Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.
Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.

Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.
Howells, G. L., et al., "Proteinase-Activated Receptor-2: Expression by Human Neutrophils", Journal of Cell Science, 1997, vol. 110, pp. 881-887.
Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.
Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.
Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.
Zhang, Y., et al., "Tissue Factor Controls the Balance of Angiogenic and Antiangiogenic Properties of Tumor Cells in Mice", J. Clin. Invest., 1994, vol. 94, pp. 1320-1327.
Green, D., et al., "Lower Mortality in Cancer Patients Treated with Low-Molecular-Weight Versus Standard Heparin", The Lancet, 1992, vol. 339, p. 1476.
Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.
Kakkar, A. K., et al., "Antithrombotic Therapy in Cancer", BMJ, 1999, vol. 3318, pp. 1571-1572.
Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.
Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.
Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.
Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.
Camerer, E., et al., "Tissue Factor- and Factor X-dependent Activation of Protease-Activated Receptor 2 by Factor VIIa", PNAS, 2000, vol. 97, No. 10, pp. 5255-5260.
Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.
Lindner, J. R., et al., "Delayed Onset of Inflammation in Protease-Activated Receptor-2-Deficient Mice", The Journal of Immunology, 2000, pp. 6504-6510.
Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.
Molino, M., et al., "Endothelial Cell Thrombin Receptors and PAR-2", The Journal of Biological Chemistry, 1997, vol. 272, No. 17, pp. 11133-11141.
Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.
Watson, D. J., et al., "Heparin-Binding Properties of the Amyloidogenic Peptides Aβ and Amylin", The Journal of Biological Chemistry, 1997, vol. 272, No. 50, pp. 31617-31624.
Tuszynski, G. P., et al., "Isolation and Characterization of Antistasin", The Journal of Biological Chemistry, 1987, vol. 262, No. 20, pp. 9718-9723.

(56) References Cited

OTHER PUBLICATIONS

Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.
Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.
Abendschein, D. R., et al., "Inhibition of Thrombin Attenuates Stenosis After Arterial Injury in Minipigs", JACC, 1996, vol. 28, No. 7, pp. 1849-1855.
Carmeliet, P., et al., "Gene Manipulation and Transfer of the Plasinogen and Coagulation System in Mice", Seminars in Thrombosis and Hemostasis, 1996, vol. 22, No. 6, pp. 525-542.
Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.
Bevilacqua, M. P., et al., "Inducible Endothelial Functions in Inflammation and Coagulation", Seminars in Thrombosis and Hemostasis, 1987, vol. 13, No. 4, pp. 425-433.
Riedl, B., et al., "Recent Developments with Oxazolidinone Antibiotics", Exp. Opin. Ther. Patents, 1999, vol. 9, No. 5, pp. 625-633.
Barbachyn, M.R., et al., "Identification of Novel Oxazolidinone (U-100480) with Potent Antimycobacterial Activity", J. Med. Chem., 1996, vol. 39, pp. 680-685.
Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.
Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med, Chem., 1996, vol. 39, pp. 673-679.
Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.
Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.
Meng, K., et al., "Effect of Acetylsalicylic Acid of Experimentally Induced Arterial Thrombosis in Rats", Naunyn-Schmiedeberg's Arch. Pharmacol., 1977, vol. 301, pp. 115-119.
Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.
Shakespeare, W. C., et al., "Palladium-Catalyzed Coupling of Lactams with Bromobenzenes", Tetrahedron Lett., 1999, vol. 40, pp. 2035*2038.
Renger, B., et al., "Direkte N-Arylierung von Amiden: Eine Verbesserung der Goldberg-Reaktion", Synthesis, 1985, pp. 856-860.
Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11 , pp. 2225-2229.
Pfeil, E., et al., "β-Aminoäthylierung von Indol and 2-methylindol", Angew Chem., 1967, vol. 79, No. 4, pp. 188-189.
Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723,.
Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.
Reppe, et al., "N-p-Merthoxyphenyl-pyrrolidon", Justus Liebigs Ann. Chem., 1955 vol. 596, p. 208.

Luvalle, J.E., et al., "Oxidation Processes. XXI.[1] The Autoxidation of the p-Phenylenediamines", J. Am. Chem. Soc., 1948, vol. 70, pp. 2223-2233.
Snyder, H.R., et al., "Imidazo[4,5-f]quinolines III: Antibacterial 7-Methyl-9-(substituted Arylamino)imidazo[4,5-f]quinolines", J. Pharm. Sci., 1977, vol. 66, pp. 1204-1406.
Adams, R., et al., "Sulfanilamide Derivatives. I", J. Am. Chem. Soc. 1939, vol. 61, pp. 2342-2349.
Khanna, I.K. , et al., "1,2-Diarylpyrroles as Potent and Selective Inhibitors of Cyclooxygenase-2", J. Med. Chem., 1997, vol. 40 , pp. 1619-1633.
Gutcait, A., et al., "Studies on Quinazolines. 6.[1] Asymmetric Synthesis of (S)-(+)- and (R)-(-)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.
Bouchet, P., et al., "σValues of N-Substitutes Azoles", J. Chem. Soc. Perkin Trans., 1974, vol. 2, pp. 449-451.
Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.
Hauptmann, J.,et al., "Synthetic Inhibitors of Thrombin and Factor Xa: From Bench to Bedside," Thrombosis Research , 93: 203-241 (1999).
Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp, 5900-5908.
Quan, M.L. The race to an orally active Factor Xa inhibitor: Recent advances. Current Opinion in Drug Discovery & Development 2004, 7, 460-469.
Greaves, et al., Novel Approaches to the Preparation of Low-Dose Solid Dosage Forms, Pharmaceutical Technology. January, pp. 60-64, (1995).
Reppe, et al., Justus Liebigs Ann. Chem. 596, 1955, p. 209-224.
Delande, S.A., "Heterocycles", Chemical Abetracts, American Chemical Society, 1979, vol. 90, pp. 663.
Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.
Bono, F., et al., "Factor Xa Activates Endothelial Cells by a Receptor Cascade Between EPR-1 and PAR-2," Arterioscler Thromb Vase Biol., Nov. 2000; pp. 1-6.
Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.
Tan, K.T. et al. Factor X inhibitors. Expert Opinion on Investig. Drugs, 2003, 12, 799-804.
Kubitza, et al., Multiple dose escalation study Investigating the pharmacodyanamics, safety, and pharmacokinetics of BAY 59-7939 an oral, direct Factor Xa inhibitor in healthy male subjects, Blood, vol. 102:11:16 Nov. 2003, p. 811a.
[Database Beilstein] Beilstein Institute for Organic Chemistry, Frankfurt-Main, DE. Database Accession No. 8822985, 1988-2001, identified from database by international examiner in PCT/EP03/14871 on Apr. 27, 2004.
Grell, W., et al., "Repaglinide and Related Hypoglycemic Benzoic Acid Derivatives", J. Med. Chem., 1998, vol. 41, pp. 5219-5246.
Artico, M. et al., "Rsearch on Compounds with Antiblastic Activity", Farmaco Ed. Sci. 1969, vol. 24, pp. 179-190.
Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.
Reppe, et al., "N-6-Aminohexyl-pyrrolidon", Justus Liebigs Ann. Chem. 1955, vol. 596, pp. 204.
Bouchet, P., et al., "A Values of N-Substitutes Azoles", J. Chem. Soc. Perkin Trans., 1974, vol. 2, pp. 449-451.

(56) References Cited

OTHER PUBLICATIONS

Surrey, a. R., et al., "The Preparation of N-Benzyl-3-Morpholones and N-Benzy1-3-Homomorpholones from N-(Hydroxyalkyl)-chloroacetamides" J. Amer. Chem, Soc., 1955, vol. 77, pp. 633-636.
Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.
Delande, S.A., "Heterocycles", Chemical Abstracts, American Chemical Society, 1979, vol. 90, pp. 663.
Bots, M., et al., Coagulation and Fibrinolysis Markers and Risk of Dementia, Haemostasis, vol. 28 (1998); pp. 216-222.
Benzakour, O., et al., "Cellular and molecular events in atherogenesis; basis for pharmocological and gene therapy approaches to stenosis," Cellular Pharmacology, 1996, vol. 3, pp. 7-22.
Kanthou, C., et al., "Cellular effects of thrombin and their signalling pathways," Cellular Pharmacology, vol. 2 (1995); pp. 293-302.
Tyrrell, D., et al., "Heparin in Inflammation: Potential Therapeutic Applications Beyond Anticoagulation," Advances in Pharmacology, vol. 46 (1999); pp. 151-208.
Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.
Bono, F., et al., "Factor Xa Activates Endothelial Cells by a Receptor Cascade Between EPR-1 and PAR-2," Arterioscler Thromb Vasc Biol., Nov. 2000; pp. 1-6.
Lala, P. et al, "Role of Nitric Oxide in tumor progression: Lessons Learned from Experimental Tumors," Cancer and Metastasis Review, vol. 17, pp. 91-106 (1998).
Golub, T., et al., Molecular Classification of Cancer Science (1999), vol. 286, 531-537.
FDA mulls drug to slow late-stage Alzheimer's [online], retrieved on Sep. 23, 2003. Retrieved from the internet, URL:http://www.cnn.com/2003/HEALTH/conditions/09/24/alzheimers.drug.ap/index.html>.
Ulllman's Encyclopedia of Industrial Chemistry, Fifth Revised Ed., Editors: Elvers, B., Hawkins, S., VCH Verlagsgesellschaft mbH, Weinheim, 1996, Ch. 5, 488-506.
Zhu, B., Scarborough, R., "Recent Advances in Inhibitors of Factor Xa in the Prothrombinase Complex," *Curr. Opinions Card. Pul. Ren. Inv. Drugs*, 1:63-87 (1999).
Uzan, A., "Antithrombotic Agents," *Emerging Drugs: The Prospect for Improved Medicines*, 3: 189-208 (1998).
Kaiser, B., "Thrombin and Factor Xa Inhibitors," *Drugs of the Future*, 23: 423-426 (1998).
Al-Obeidi, F., Ostrem, J., "Factor Xa Inhibitors," *Expert Opin. Therapeutic Patents*, 9: 931-953 (1999).
Al-Obeidi, F., Ostrem, J., "Factor Xa Inhibitors by Classical and Combinatorial Chemistry," *DDT*, 3: 223-231 (May 1998).
Hauptmann, J.,et al., "Synthetic Inhibitors of Thrombin and Factor Xa: From Bench to Bedside," *Thrombosis Research*, 93: 203-241 (1999).
Pschyrembel, Klinisches Worterbuch, 257. Auflage, 1994, Walter de Gruyter Verlag, pp. 199-200, Stichwort "Blutgerinnung.".
Pschyrembel, Klinisches Worterbuch, 257. Auflage, 1994, Walter de Gruyter Verlag, p, 610, Stichwort "Heparin.".
Rompp Lexikon Chemie, Ver. 1.5, 1998, Georg Thieme Verlag Stuttgart, Stichwort "Heparin.".
Pschyrembel, Klinisches Worterbuch, 257. Auflage, 1994, Walter de Gruyter Verlag, p. 292, Stichwort "Cumarinderivate.".
Becker, M.R., et al., "Synthesis, Sar and in Vivo Activity of Novel Thienopyridine Sulfonamide Pyrrolidininones as Factor Xa Inhibitors," *Bioorganic and Medicinal Chemistry Letters*, 9: 2753-2758 (1999).
Linder, J., et al., "Delayed Onset of Inflammation in Protease-Activated Receptor-2-Deficient Mice," J. Immunology, 2000, pp. 6504-6510.
Cirino, G. et al, Inflammation-Coagulation Network: Are Serine Protease receptors the knot?; Tips; 2000, vol. 21, pp. 170-172.

Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp. 5900-5908.
Caira, M. Crystalline Polymorphism Of Organic Compounds. Springer Verlag Berlin Heidelberg 198, 1998, pp. 163-208.
Hancock, B. et al. Characteristics and Significance of the Amorphous State in Pharmaceutical Systems. Journal of Pharmaceutical Science. 86, 1 (1997), pp. 1-12.
Gilligan, D.M. et al. The Management of Atrial Fibrillation. The American Journal of Medicine, vol. 101, (4) 1996, 413-421.
Kubitza, D. et al. Novel factor Xa inhibitors for prevention and treatment of thromboembolic diseases. Expert Opinion on Investig. Drugs, vol. 15, (8) 2006, pp. 843-855.
Sinha, U. et al. Antithrombotic and hemostatic capacity of factor Xa versus thrombin inhibitors in models of venous and arteriovenous thrombosis. European Journal of Pharmacology 2000, 395, 51-59.
Betz, A. Recent advances in Factor Xa inhibitors, Expert Opinion Ther. Patents, 2001, 11(6), 1007-1017.
Ruef, J. et al. New antithrombotic drugs on the horizon. Expert Opinion on Investig. Drugs 2003, 12, 781-797.
Samama, M.M. Synthetic direct and indirect factor Xa inhibitors. Thrombosis Research 2002, 106, V267-V273.
Duan, M.L. The race to an orally active Factor Xa inhibitor: Recent advances. Current Opinion in Drug Discovery & Development 2004, 7, 460-469.
The Ephesus Study, Blood 2000, 96, 490a.
The Penthifra Study, Blood 2000, 96, 490a.
The Pentamaks Study, Blood 2000, 96, 490a-491a.
Leadley, R.J. Coagulation Factor Xa Inhibition: Biological Background and Rationale. Current Topics in Medicinal Chemistry 2001, 1, 151-159.
The Penthathlon 2000 Study, Blood 2000, 96, 491a.
Williams, E.M. Vaughan. Classificating anti-arrhythimic drugs. In: Cardiac Arrythias-Proceedings of a symposium, sandoe E., soedertaeje: Astra (1970), pp. 449-469.
Stroke: Warning Signs and Tips for Prevention [online], retrieved Aug. 20, 2007 from the internet at http://familydoctor.org/online/famdocen/home/common/heartdisease/basics/290.html.
Kubitza, et al., Multiple dose escalation study Investigating the pharmacodyanamics, safety, and pharmacokinetics of BAY 59/7939 an oral, direct Factor Xa inhibitor in healthy male subjects, Blood, vol. 102:11:16 Nov. 2003, p. 811a.
Kubitza, et al., Abstract 3010, Single dose escalation study investigating the pharmacodyanamlcs, safety, and pharmacokinetics of BAY 59/7939 an oral, direct Factor Xa inhibitor in healthy male subjects, Blood, vol. 102:11. Nov. 16, 2003, p. 813a.
Lerk, et al., Effect of Hydrophilization Drugs on Release Rat from Capsules, J. of Pharma. Sciences, 67(7), pp. 935-939 (1978).
Lerk, et al., in Vitro and in Vivo Availability of Hydrophilized Phenytoin from Capsules, J. of Pharma. Sciences, 68(5), pp. 634-638 (1979).
Greaves, et al., Novel Approaches to the Preparation of Low-Dose Solid Dosage Forms, Pharmaceutical Technology. January pp. 60-64, (1995).
Reppe, et al., Justus Liebigs Ann. Chem. 596, 1955, p. 209.
Al-Obeidi, F., Ostrem, J., "Factor Xa Inhibitors by Classical and Combinatorial Chemistry," *DDT*, 3: 223-231 (May 1998).
Rompp Lexikon Chemie, Ver, 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.
Pschyrembel, Klinisches Worterbuch, 257. Auflage, 1994, Walter de Gruyter Verlag, p. 610, Stichwort "Heparin.".
Cirino, G. et al. Inflammation-Coagulation Network: Are Serine Protease receptors the knot?; Tips; 200, vol. 21, pp. 170-172, 2000.
Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl)methyl)thiophene-2-carboxamide (BAY 597939): An Oral, Direct Factor Xa Inhibitor. J. Med. Chem. 48, Sep. 22, 2005, pp. 5900-5908.

(56) References Cited

OTHER PUBLICATIONS

Hancock, B. et al. Characteristics and Significance of the Amorphous State in Pharmaceutical Systems. Journal Of Pharmaceutical Science. 86, 1 (Jan. 1997), pp. 1-12.

Betz, A. Recent advances in Factor Xa inhibitors, Expert Opinion Ther. Patents 2001, 11(6), 1007-1017.

Tan, K.T. et al. Factor X inhibitors. Expert Opinion on Investig. Drugs 2003, 12, 799-804.

Kubitza, et al., Multiple dose escalation study Investigating the pharmacodyanamics, safety, and pharmacokinetics of BAY 59/7939 An oral, direct Factor Xa inhibitor in healthy male subjects, Blood, vol. 102:11: Nov. 16, 2003, p. 811a.

Kubitza, et al,, Abstract 3010, Single dose escalation study investigating the pharmacodyanamlcs, safety, and pharmacokinetics of BAY 59/7939 an oral, direct Factor Xa inhibitor in healthy male subjects, Blood, vol. 102:11. Nov. 16, 2003, p. 813a.

Greaves, et al., Novel Approaches to the Preparation of Low-Dose Solid Dosage Forms,Pharmaceutical Technology. January pp. 60-64, (1995).

\* cited by examiner

SOLID ORALLY ADMINISTERABLE PHARMACEUTICAL DOSAGE FORMS WITH RAPID ACTIVE PRINCIPLE RELEASE

RELATED APPLICATIONS

This application is a national stage application (under 35 U.S.C. 371) of PCT/EP2006/009178 filed Sep. 21, 2006, which claims benefit of German application 10 2005 047 561.2 filed Oct. 4, 2005.

The present invention relates to solid pharmaceutical dosage forms which can be administered orally and comprise 5-chloro-N-({(5S)-2-oxo-3-[4-(3-oxo-4-morpholinyl)phenyl]-1,3-oxazolidin-5-yl}methyl)-2-thiophenecarboxamide in amorphous form and/or thermodynamically metastable crystal modification and have rapid release of active ingredient, and to process for the production thereof, the use thereof as medicament, the use thereof for the prophylaxis, secondary prophylaxis and/or treatment of disorders, and to the use thereof for producing a medicament for the prophylaxis, secondary prophylaxis and/or treatment of disorders.

5-Chloro-N-({(5S)-2-oxo-3-[4-(3-oxo-4-morpholinyl)phenyl]-1,3-oxazolidin-5-yl}methyl)-2-thiophenecarboxamide (I) is a low molecular weight inhibitor of coagulation factor Xa which can be administered orally and can be employed for the prophylaxis, secondary prophylaxis and/or treatment of various thromboembolic disorders (concerning this, see WO 01/47919, the disclosure of which is hereby incorporated by reference). When active ingredient (I) is mentioned hereinafter, this encompasses all crystal modifications and the amorphous form of 5-chloro-N-({(5S)-2-oxo-3-[4-(3-oxo-4-morpholinyl)phenyl]-1,3-oxazolidin-5-yl}methyl)-2-thiophenecarboxamide (I) and the respective hydrates, solvates and cocrystals.

It is necessary in the development of formulations to take account of the physicochemical and biological properties of the active ingredient (I), for example the relatively low solubility in water (about 7 mg/l; 25° C.) and the relatively high melting point of about 230° C. of the active ingredient (I) in the crystal modification in which the active ingredient (I) is obtained when prepared by the route described in Example 44 of WO 01/47919 (Chem. Abstr. 2001, 135, 92625) and which is referred to hereinafter as crystal modification I.

WO 2005/060940 describes pharmaceutical dosage forms which comprise the active ingredient (I) in hydrophilized form. Preference is given in this connection to rapid-release tablets which have a Q value (30 minutes) of 75% in the USP (United States Pharmacopeia) release method with apparatus 2 (paddle).

It has surprisingly now been found that dosage forms which comprise active ingredient (I) in amorphous form and/or in the form of thermodynamically metastable crystal modifications display improved bioavailability.

The present invention relates to solid dosage forms which can be administered orally and have rapid release of active ingredient and comprise 5-chloro-N-({(5S)-2-oxo-3-[4-(3-oxo-4-morpholinyl)phenyl]-1,3-oxazolidin-5-yl}methyl)-2-thiophenecarboxamide (I), characterized in that they comprise active ingredient (I) in amorphous form and/or thermodynamically metastable crystal modification, and that 80% of the active ingredient (I) are released over a period not exceeding 2 hours in the USP release method with apparatus 2 (paddle; 75 rpm). The further conditions of these in vitro release investigations according to USP release method are described in the experimental section (sink conditions). The amount of 80% of active ingredient (I) released is based on the total amount of active ingredient (I) present in the dosage form.

Preference is given to solid pharmaceutical dosage forms which can be administered orally and have rapid release of active ingredient and comprise 5-chloro-N-({(5S)-2-oxo-3-[4-(3-oxo-4-morpholinyl)phenyl]-1,3-oxazolidin-5-yl}methyl)-2-thiophenecarboxamide (I), characterized in that they comprise active ingredient (I) in amorphous form and that 80% of active ingredient (I) are released over a period not exceeding 2 hours in USP release method with apparatus 2 (paddle; 75 rpm).

In a preferred embodiment of the present invention, 80% of active ingredient (I) are released in a period not exceeding 1 hour in USP release method with apparatus 2 (paddle; 75 rpm).

The active ingredient (I) may be present in the dosage forms according to the invention partly or completely in amorphous form and/or thermodynamically metastable crystal modification. The dosage forms according to the invention preferably comprise active ingredient (I) in amorphous form and/or in the form of metastable crystal modifications in an amount of at least 50%, particularly preferably more than 50%, in particular at least 90%, based on the total amount of active ingredient (I) present.

The active ingredient (I) can preferably be present in the dosage forms according to the invention partly or completely in amorphous form. The dosage forms according to the invention preferably comprise active ingredient (I) in amorphous form in an amount of at least 50%, particularly preferably more than 50%, in particular at least 90%, based on the total amount of active ingredient (I) present.

In a preferred embodiment of the present invention, the partial or complete presence of the active ingredient (I) in amorphous form and/or in the form of one or more thermodynamically metastable crystal modifications also increases the active ingredient solubility, besides a rapid release rate. In this embodiment too, the dosage forms according to the invention comprise active ingredient (I) in amorphous form and/or in the form of metastable crystal modifications preferably in an amount of at least 50%, particularly preferably more than 50%, in particular at least 90%, based on the total amount of active ingredient (I) present. The increase in the active ingredient solubility or "supersaturation" is demonstrated in vitro release tests: The term "supersaturation" means in this connection that the formulations according to the invention display a release of active ingredient which is a factor of at least 1.5 times higher under the in vitro release conditions defined in the experimental section under non-sink conditions with a dose of 20 mg active ingredient (I) after one hour compared with crystalline micronized active ingredient (I) in crystal modification I. In this embodiment, the dosage forms according to the invention comprise active ingredient (I) in a total amount of 20 mg and release an amount of active ingredient (I) in a period of one hour in USP release method with apparatus 2 (paddle) which is a factor of at least 1.5 times higher compared with 20 mg of micronized crystalline active ingredient (I) in crystal modification I. If, for example, the micronized active ingredient (I) exhibits a release of 40% (8 mg) after one hour under these conditions, the formulations according to the invention show release levels of at least 60% (12 mg). The micronized active ingredient (I) in this case has an average particle size $X_{50}$ value (50% proportion) of from 1 to 8 μm and an $X_{90}$ value (90% proportion) of less than 20 μm.

In a preferred embodiment of the present invention, the partial or complete presence of the active ingredient (I) in amorphous form also increases the active ingredient solubility, besides a rapid release rate. In this embodiment too, the dosage forms according to the invention comprise active ingredient (I) in amorphous form preferably in an amount of at least 50%, particularly preferably more than 50%, in particular at least 90%, based on the total amount of active ingredient (I) present. The increase in the active ingredient solubility or "supersaturation" is demonstrated in vitro release tests: The term "supersaturation" means in this connection that the formulations according to the invention display a release of active ingredient which is a factor of at least 1.5 times higher under the in vitro release conditions defined in the experimental section under non-sink conditions with a dose of 20 mg active ingredient (I) after one hour compared with crystalline micronized active ingredient (I) in crystal modification I. In this embodiment, the dosage forms according to the invention comprise active ingredient (I) in a total amount of 20 mg and release an amount of active ingredient (I) in a period of one hour in USP release method with apparatus 2 (paddle) which is a factor of at least 1.5 times higher compared with 20 mg of micronized crystalline active ingredient (I) in crystal modification I. If, for example, the micronized active ingredient (I) exhibits a release of 40% (8 mg) after one hour under these conditions, the formulations according to the invention show release levels of at least 60% (12 mg). The micronized active ingredient (I) in this case has an average particle size $X_{50}$ value (50% proportion) of from 1 to 8 μm and an $X_{90}$ value (90% proportion) of less than 20 μm.

It is possible to employ for producing the pharmaceutical dosage forms according to the invention all crystal modifications and the amorphous form of 5-chloro-N-({(5S)-2-oxo-3-[4-(3-oxo-4-morpholinyl)phenyl]-1,3-oxazolidin-5-yl}methyl)-2-thiophenecarboxamide (I) and the respective hydrates, solvates and cocrystals.

Various pharmaceutically suitable production methods are possible for amorphization of active ingredients and for generating thermodynamically metastable crystal modifications, and for stabilizing these active ingredient forms in formulations. The dissolving method, the melting method or a combination of these two methods are frequently employed [Chiou, W. L.; Riegelman, S., "Pharmaceutical Applications of Solid Dispersion Systems", Journal of Pharmaceutical Sciences 60 (1971), 1281-1302; Ford, J. L., "The Current Status of Solid Dispersions", Pharm. Acta Hely, 61 (1986), 69-88; Rasenack, N., "Poorly Water-soluble Drugs for Oral Delivery—A Challenge for Pharmaceutical Development, Part III: Drug delivery systems containing the drug molecularly dispersed/Aspects on in vitro and in vivo characterization", Pharmazeutische Industrie 67, No. 5 (2005), 583-591].

The dissolving method, in which an active ingredient and excipient(s) employed where appropriate, such as, for example, polyvinylpyrrolidone, are dissolved and then further processed is less suitable for the crystalline active ingredient (I) in the thermodynamically stable crystal modification I, because it has only a limited solubility in pharmaceutically suitable organic solvents such as, for example, acetone or ethanol, and therefore disproportionately large amounts of solvent must be used. Pure acetic acid forms an exception, being a suitable solvent for the crystalline active ingredient (I)—a suitable production method is described in the experimental section.

The active ingredient (I) is present in the mixture present after the dissolving method according to the invention preferably in a concentration of from 0.1 to 30%, particularly preferably from 0.1 to 20%, in particular from 5 to 15%, based on the total mass of the dissolved components.

The method preferred according to the invention for amorphizing active ingredient (I) and for generating thermodynamically metastable crystal modifications, and for stabilizing the amorphous state of active ingredient (I) in the pharmaceutical preparations is the melting method, in which an active ingredient is melted together with or in one or more suitable excipients.

Examples of excipients suitable for the melting method are urea, citric acid, stearic acid, sugars, sugar alcohols such as, for example, mannitol or xylitol and hydrophilic polymers such as, for example, polyethylene glycols (PEG), polyethylene oxides, polyoxyethylene-polyoxypropylene block copolymers and vinylpyrrolidone-vinyl acetate copolymers, hydroxypropylcellulose (HPC), saturated polyglycolized glycerides (Gelucire, Gattefosse) or mixtures of these excipients. Preferred excipients are polyethylene glycols, mixtures of polyethylene glycols and mixtures of one or more polyethylene glycols with one or more other suitable excipients, particular preferably polyethylene glycols and mixtures of polyethylene glycols, in particular polyethylene glycols. The active ingredient (I) is added to the molten excipient or excipient mixture, and the temperature is raised until a clear melt is present, or the active ingredient (I) and the excipient(s) are initially mixed and then melted. The melting is followed by cooling and subsequent comminution to result in a powder or granules, which can also be referred to as "solid solution". Alternatively, the melt can after comminution for example be packed into capsules or as sachet, where appropriate after admixture of suitable pharmaceutical excipients. It must be ensured, by choice of a suitable formulation and suitable production parameters, in this melting method that the degradation of active ingredient does not exceed pharmaceutically acceptable limits during the melting process. This is a difficult task with a melting point of about 230° C. for the active ingredient (I) in crystal modification I, because significant rates of decomposition of the active ingredient and/or the excipients are usually to be expected in this high temperature range.

The active ingredient (I) is present in the mixture present after the melting process according to the invention preferably in a concentration of from 0.1 to 30%, particularly preferably from 0.1 to 20%, especially from 5 to 15%, based on the total mass of the melt.

The melt extrusion method is particularly preferred for producing pharmaceutical dosage forms comprising active ingredient (I) in amorphous form or metastable crystal modifications [Breitenbach, J., "Melt extrusion: From process to drug delivery technology", European Journal of Pharmaceutics and Biopharmaceutics 54 (2002), 107-117; Breitenbach, J., "Feste Lösungen durch Schmelzextrusion—ein integriertes Herstellkonzept", Pharmazie in unserer Zeit 29 (2000), 46-49].

It must also be ensured in this production method, through choice of a suitable formulation and suitable production parameters, that the degradation of active ingredient does not exceed pharmaceutically acceptable limits.

The melt extrusion method for preparing the active ingredient (I) in amorphous form or in the form of metastable crystal modifications is preferably carried out in the presence of a polymer such as, for example, polyvinylpyrrolidone (PVP), polyethylene glycol, polymethacrylate, polymethylmethacrylate, polyethylene oxide, polyoxyethylene-polyoxypropylene block copolymers, vinylpyrrolidone-vinyl acetate copolymers or a cellulose ether such as, for example, hydroxypropylcellulose (HPC) or of mixtures of various polymers. The preferred polymer in this connection is hydroxypropylcellulose (HPC), polyvinylpyrrolidone (PVP)

or a mixture of HPC and PVP. Hydroxypropylcellulose (HPC) or polyvinylpyrrolidone (PVP) is particularly preferred.

The proportion of polymer in the melt extrudate is preferably according to the invention at least 40% of the total mass of the melt extrudate.

The active ingredient (I) is preferably present according to the invention in the melt extrudate in a concentration of from 0.1 to 20%, in particular from 5 to 15%, based on the total mass of the melt extrudate.

It has proved advantageous in the melt extrusion method for preparing or stabilizing the active ingredient (I) in amorphous form to add one or more pharmaceutically suitable substances to depress the melting point of the active ingredient or as plasticizer of the polymer, in order to facilitate processing and reduce the degradation of active ingredient taking place during the extrusion process.

These pharmaceutically suitable substances are preferably added according to the invention in a concentration of from 0.2 to 40%, based on the total mass of the melt extrudate.

Examples suitable for this purpose are urea, polymers such as polyethylene glycol, polymethacrylates, polymethylmethacrylates, polyethylene oxide, polyoxyethylene-polyoxypropylene block copolymers, vinylpyrrolidone-vinyl acetate copolymers, saturated polyglycolized glycerides (Gelucire, Gattefosse) or sugar alcohols such as, for example, erythritol, maltitol, mannitol, sorbitol and xylitol. Sugar alcohols are preferably employed. It must be ensured in this connection, by choice of suitable preparation parameters, that the active ingredient (I) is converted as completely as possible into the amorphous or thermodynamically metastable state in order to increase the active ingredient solubility.

The product which has been obtained for example by the dissolving method, the melting or the melt extrusion method and which comprises active ingredient (I) in amorphous form or metastable crystal modification(s) can be further processed in various ways: it can for example be comminuted and administered as powder or granules, where appropriate after packing as sachet or in capsules. It is moreover possible to add conventional pharmaceutical excipients such as, for example, fillers, flow regulators, adsorbents, wetting agents, flavours and colours.

The product comprising the active ingredient (I) in amorphous form or metastable crystal modifications may additionally be further processed to tablet formulations. It can for this purpose be cut, ground and mixed with conventional tabletting excipients such as fillers and dry binders (for example cellulose powder, microcrystalline cellulose, silicified microcrystalline cellulose, dicalcium phosphate, tricalcium phosphate, magnesium trisilicate, mannitol, maltitol, sorbitol, xylitol, lactose, dextrose, maltose, sucrose, glucose, fructose or maltodextrins), disintegration promoters/disintegrants (for example carboxymethylcellulose, croscarmellose (crosslinked carboxymethylcellulose), crospovidone (crosslinked polyvinylpyrrolidone), L-HPC (low-substituted hydroxypropylcellulose), sodium carboxymethylstarch, sodium glycolate of potato starch, partially hydrolysed starch, wheat starch, maize starch, rice starch or potato starch), lubricants, glidants and flow regulators such as fumaric acid, stearic acid, magnesium stearate, calcium stearate, sodium stearyl fumarate, high molecular weight fatty alcohols, polyethylene glycols, starch (wheat, rice, maize or potato starch), talc, colloidal silicon dioxide, magnesium oxide, magnesium carbonate or calcium silicate, adsorbents, flavours and colours, and compressed to tablets, and the latter can then where appropriate also be coated. Suitable materials for a photoprotective and/or colouring coating are for example polymers such as polyvinyl alcohol, hydroxypropylcellulose and/or hydroxypropylmethylcellulose, where appropriate combined with suitable plasticizers such as, for example, polyethylene glycol or polypropylene glycol and pigments such as, for example, titanium dioxide or iron oxides. The tablets are preferably tablets which disintegrate rapidly and have a disintegration time not exceeding 30 minutes.

The present invention further relates to a process for producing the tablet formulation according to the invention, where a solid solution or extrudate comprising an active ingredient (I) in amorphous form or metastable crystal modification is produced with the aid of the dissolving method, preferably with the aid of the melting method, very particularly preferably with the aid of melt extrusion, and is then ground, mixed with further pharmaceutical excipients known to the skilled person and packed into capsules or as sachet, or mixed with further tabletting aids (see above) known to the skilled person and then compressed preferably by direct tabletting to tablets which can finally be covered with a coating. Active ingredient (I) is particularly preferably present in amorphous form.

A product which has been obtained by the melting process and comprises active ingredient (I) in amorphous form and/or metastable crystal modification can furthermore be produced in the form of multiparticulate dosage forms. The term "multiparticulate dosage forms" means according to the invention those formulations which consist of a plurality of small particles such as, for example, spherical granules (pellets) or minitablets. The diameter of these particles is ordinarily from 0.5 to 3.0 mm. The cut and rounded extrudates or small-format tablets (minitablets with diameter not exceeding 3 mm) can be coated where appropriate and packed in capsules or prepared as sachet. A further possibility consists of further processing to larger tablets which, after contact with water/gastric juice, release the primary granules/pellets by rapid disintegration. Active ingredient (I) is particularly preferably present in amorphous form.

The present invention further relates to pharmaceutical dosage forms, preferably capsules, sachets or tablets, comprising the multiparticulate dosage forms described above.

The present invention further relates to a process for producing the multiparticulate pharmaceutical dosage forms according to the invention, where an extrudate comprising active ingredient (I) in amorphous form and/or thermodynamically metastable crystal modification is preferably obtained by melt extrusion. In a preferred embodiment of the present invention, a multiparticulate dosage form in pellet form is produced directly by cutting this extrudate strand and, where appropriate, subsequent rounding. The pellets obtained in this way can then be covered with a coating and packed in capsules or as sachet. Active ingredient (I) is particularly preferably present in amorphous form.

The present invention further relates to medicaments comprising a solid pharmaceutical dosage form according to the invention which can be administered orally, comprises active ingredient (I) in amorphous form and/or thermodynamically metastable crystal modification(s) and has rapid release of active ingredient. Active ingredient (I) is particularly preferably present in amorphous form.

The present invention further relates to the use of the solid pharmaceutical dosage form according to the invention which can be administered orally and has rapid release of active ingredient, and which comprises amorphous and/or thermodynamically metastable active ingredient (I) for the prophylaxis, secondary prophylaxis and/or treatment of disorders, in particular of arterial and/or venous thromboembolic disorders such as myocardial infarction, angina pectoris (including unstable angina), reocclusions and restenoses following angioplasty or aortocoronary bypass, stroke, transient ischaemic attacks, peripheral arterial occlusive diseases, pulmonary embolisms or deep vein thromboses. Active ingredient (I) is particularly preferably present in amorphous form.

The present invention further relates to the use of the solid pharmaceutical dosage form according to the invention which can be administered orally, comprises the amorphous and/or thermodynamically metastable active ingredient (I) and has rapid release of active ingredient for producing a medicament for the prophylaxis, secondary prophylaxis and/or treatment of disorders, in particular of arterial and/or venous thromboembolic disorders such as myocardial infarction, angina pectoris (including unstable angina), reocclusions and restenoses following angioplasty or aortocoronary bypass, stroke, transient ischaemic attacks, peripheral arterial occlusive diseases, pulmonary embolisms or deep vein thromboses. Active ingredient (I) is particularly preferably present in amorphous form.

The present invention further relates to the use of 5-chloro-N-({(5S)-2-oxo-3-[4-(3-oxo-4-morpholinyl)phenyl]-1,3-oxazolidin-5-yl}methyl)-2-thiophenecarboxamide (I) for producing a solid pharmaceutical dosage form according to the invention which can be administered orally and has rapid release of active ingredient.

The present invention further relates to a method for the prophylaxis, secondary prophylaxis and/or treatment of arterial and/or venous thromboembolic disorders by administering a solid pharmaceutical dosage form according to the invention which can be administered orally, comprises active ingredient (I) in amorphous form and/or thermodynamically metastable crystal modification and has rapid release of active ingredient. Active ingredient (I) is particularly preferably present in amorphous form.

The invention is explained in more detail below by preferred exemplary embodiments, to which it is not restricted, however. Unless indicated otherwise, all statements of amounts below refer to percentages by weight.

EXPERIMENTAL SECTION

The in vitro release investigations are carried out by USP release method with apparatus 2 (paddle) at a temperature of 37° C. The speed of rotation of the stirrer is 75 rpm (revolutions per minute) in 900 ml of an acetate buffer solution of pH 4.5, which is prepared from 29.9 g of sodium acetate trihydrate and 16.6 ml of glacial acetic acid in 10 l of water.

The investigations in this connection take place under sink or non-sink conditions.

Sink conditions: The active ingredient release rate is determined under sink conditions. Depending on the active ingredient dose to be tested it is possible to employ a surfactant, preferably sodium lauryl sulphate, for setting up the sink conditions. The solubility of the medium for the active ingredient (I) is adjusted where appropriate by adding surfactant, preferably sodium lauryl sulphate, so that it is a factor of 3 to 10 higher than the saturation solubility of the active ingredient dose to be tested.

Non-sink conditions: The investigations for examining the supersaturation (increase in solubility) take place without addition of a surfactant and with a dose of 20 mg of active ingredient (I) to be released.

The in vitro release investigations described below were carried out under non-sink conditions in order to demonstrate the supersaturation behaviour of the exemplary formulations.
Comparative Formulations:

To illustrate the supersaturation behaviour of exemplary formulations 1 to 6 (see below), as comparison the in vitro release (non-sink conditions) of the micronized crystalline active ingredient (I) in the thermodynamically stable crystal modification I and of a rapid-release tablet formulation produced by fluidized bed granulation and comprising micronized crystalline active ingredient (I) in crystal modification I were determined.
Comparative Formulation 1.1

In vitro release (non-sink conditions) of the micronized ($X_{50}$=4 µm; $X_{90}$=10 µm) crystalline active ingredient (I) in crystal modification I; active ingredient dose 20 mg:

| | Time [min] | | | |
|---|---|---|---|---|
| | 15 | 30 | 60 | 90 |
| Release [%] | 23 | 34 | 41 | 44 |

(USP paddle, 75 rpm, 900 ml of acetate buffer of pH 4.5)

Comparative Formulation 1.2

In vitro release (non-sink conditions) of a tablet formulation comprising 10 mg of micronized crystalline active ingredient (I) in crystal modification I; active ingredient dose 20 mg by application of 2 tablets per vessel:

| | Time [min] | | | |
|---|---|---|---|---|
| | 15 | 30 | 60 | 90 |
| Release [%] | 46 | 50 | 52 | 52 |

(USP paddle, 75 rpm, 900 ml of acetate buffer of pH 4.5)

The tablet formulation took the form of tablet B described in terms of composition and production in section 5.1 in the experimental section in WO 2005/060940 and which had then been coated, with the following composition of the coating (in mg/tablet):

| Hydroxypropylmethylcellulose 15 cp | 1.5 mg |
| Polyethylene glycol 3350 | 0.5 mg |
| Titanium dioxide | 0.485 mg |
| Iron oxide red | 0.015 mg |

Exemplary Formulation 1:

Active ingredient melt in PEG 6000 comprising active ingredient (I) in thermodynamically metastable crystal modification:

| Active ingredient (I), micronized (MOD 1) | 200 g |
| Polyethylene glycol 6000 | 1.800 g |
| | 2.000 g |

Production:

Polyethylene glycol is melted in a heatable reaction vessel (with stirrer and temperature sensor). After a temperature of about 210° C. is reached, the micronized active ingredient (I) is added and heating is continued. After a temperature of 220-230° C. is reached, the clear melt is discharged into foils and these are cooled with the aid of dry ice. Grating is followed by comminution in an impact mill to result in a product in powder form.

In vitro release (non-sink conditions) of exemplary formulation 1 (active ingredient dose 20 mg):

|  | Time [min] | | | |
| --- | --- | --- | --- | --- |
|  | 15 | 30 | 60 | 90 |
| Release [%] | 48 | 71 | 82 | 87 |

(USP paddle, 75 rpm, 900 ml of acetate buffer of pH 4.5)

It is clear that exemplary formulation 1 displays a distinctly increased solubility (supersaturation) compared with micronized active ingredient (I) (comparison 1.1). A solubility higher by a factor of 2 is detectable after 1 hour.

Exemplary Formulation 2:

Melt extrudate with hydroxypropylcellulose comprising amorphous active ingredient (I):

| Active ingredient (I), micronized (MOD 1) | 450 g |
| --- | --- |
| Hydroxypropylcellulose (type HPC-M, Nisso) | 3900 g |
| Xylitol | 900 g |
|  | 5250 g |

Production:

Micronized active ingredient (I), hydroxypropylcellulose and xylitol are mixed and processed in a twin screw extruder (Leistritz Micro 18 PH) with a die diameter of 2 mm. The mixture is extruded is with a throughput of about 1 kg/h and the following temperatures of the heating zones: 20° C. (zone 1), 100° C. (zone 2), 174° C. (zone 3) and 194° C. (zones 4-8 and die outlet). The resulting extrudate strand is cut into pieces about 1 mm in size and then ground in an impact mill.

In vitro release (non-sink conditions) of exemplary formulation 2 (active ingredient dose 20 mg; sieve fraction<315 μm):

|  | Time [min] | | | |
| --- | --- | --- | --- | --- |
|  | 15 | 30 | 60 | 90 |
| Release [%] | 36 | 66 | 85 | 90 |

(USP paddle, 75 rpm, 900 ml of acetate buffer of pH 4.5)

It is clear that exemplary formulation 2 displays a distinctly increased solubility (supersaturation) compared with micronized active ingredient (I) (comparison 1.1). A solubility higher by a factor of 2.1 is detectable after 1 hour.

Exemplary Formulation 3:

Melt extrudate with polyvinylpyrrolidone comprising amorphous active ingredient (I):

| Active ingredient (I), micronized (MOD 1) | 220 g |
| --- | --- |
| Polyvinylpyrrolidone (Kollidon 25, BASF) | 1985 g |
| Xylitol | 245 g |
|  | 2450 g |

Production:

Micronized active ingredient (I), polyvinylpyrrolidone and xylitol are mixed and processed in a twin screw extruder (Leistritz Micro 18 PH) with a die diameter of 2 mm. The mixture is extruded with a throughput of about 1 kg/h and the following temperatures of the heating zones: 20° C. (zone 1), 100° C. (zone 2), 180° C. (zone 3) and 200° C. (zones 4-8 and die outlet). The resulting extrudate strand is cut into pieces about 1 mm in size and then ground in an impact mill.

In vitro release of exemplary formulation 3 (active ingredient dose 20 mg; sieve fraction<315 μm):

|  | Time [min] | | | |
| --- | --- | --- | --- | --- |
|  | 15 | 30 | 60 | 90 |
| Release [%] | 66 | 93 | 97 | 97 |

(USP paddle, 75 rpm, 900 ml of acetate buffer of pH 4.5)

It is clear that exemplary formulation 3 displays a distinctly increased solubility (supersaturation) compared with micronized active ingredient (I) (comparison 1.1). A solubility higher by a factor of 2.4 is detectable after 1 hour.

Exemplary Formulation 4:

Tablets comprising active ingredient (I) in metastable crystal modification in the form of a PEG melt Composition for 10 mg active ingredient (I) containing tablets (mg/tablet):

| Active ingredient (I)-PEG 6000 melt (see Example 1) | 100 mg* |
| --- | --- |
| Microcrystalline cellulose | 270 mg |
| Mannitol (Pearlitol SD 200, Roquette) | 200 mg |
| Croscarmellose (Ac-Di-Sol, FMC) | 20 mg |
| Colloidal silicon dioxide (Aerosil 200, Degussa) | 4 mg |
| Magnesium stearate | 6 mg |
|  | 600 mg |

(*Amount is adapted according to the current active ingredient content; compensating substance is microcrystalline cellulose)

Production:

An active ingredient (I)-PEG melt is produced as described in Example 1. After sieving (0.63 mm), the further excipients (see above table) are admixed, and this mixture is compressed in a tablet press to tablets in oblong format 17×7 mm with a flexural strength of about 40 N.

In vitro release (non-sink conditions) of exemplary formulation 4 (active ingredient dose 20 mg; 2 tablets/vessel):

|  | Time [min] | | | |
| --- | --- | --- | --- | --- |
|  | 15 | 30 | 60 | 90 |
| Release [%] | 65 | 78 | 88 | 93 |

(USP paddle, 75 rpm, 900 ml of acetate buffer of pH 4.5)

It is clear that exemplary formulation 4 displays a distinctly increased solubility (supersaturation) compared with micronized active ingredient (I) (comparison 1.1). A solubility higher by a factor of 2.1 is detectable after 1 hour.

Exemplary Formulation 5:

Tablets comprising amorphous active ingredient (I) in the form of an HPC melt extrudate Composition for 10 mg active ingredient (I) containing tablets (mg/tablet):

| | |
|---|---|
| Active ingredient (I)-HPC extrudate (see Example 2) | 117 mg* |
| Microcrystalline cellulose | 253 mg |
| Lactose (Tablettose, Meggle) | 200 mg |
| Croscarmellose (Ac-Di-Sol, FMC) | 20 mg |
| Colloidal silicon dioxide (Aerosil 200, Degussa) | 4 mg |
| Magnesium stearate | 6 mg |
| | 600 mg |

(*Amount is adapted according to the current active ingredient content; compensating substance is microcrystalline cellulose)

Production:

An active ingredient (I)-HPC melt is produced as described in Example 2. After sieving (0.4 mm), the further excipients (see above table) are admixed, and this mixture is compressed in a tablet press to tablets in oblong format 17×7 mm with a flexural strength of about 40 N.

In vitro release (non-sink conditions) of exemplary formulation 5 (active ingredient dose 20 mg; 2 tablets/vessel):

| | Time [min] | | | |
|---|---|---|---|---|
| | 15 | 30 | 60 | 90 |
| Release [%] | 100 | 101 | 101 | 101 |

(USP paddle, 75 rpm, 900 ml of acetate buffer of pH 4.5)

It is clear that exemplary formulation 5 displays a distinctly increased solubility (supersaturation) compared with micronized active ingredient (I) (comparison 1.1). A solubility which is higher by a factor of 2.5 is detectable after 1 hour.

Exemplary Formulation 6:

Granules produced by the dissolving method with polyvinylpyrrolidone containing active ingredient (I) in amorphous form:

| | |
|---|---|
| Active ingredient (I), micronized (MOD 1) | 4.0 g |
| Polyvinylpyrrolidone 25 | 28.0 g |
| Glacial acetic acid (acetic acid pure) | 140.0 g |
| | 172.0 g |

Production:

Active ingredient (I) is dissolved in glacial acetic acid at a temperature of about 90-100° C. in a rotary evaporator, and the solvent is then distilled out in vacuo. The remaining mass is coarsely comminuted and transferred into a vacuum drying oven. Drying takes place in vacuo at a temperature of 100-120° C. for about 48 hours. The granules are ground in a mortar and sieved (<1 mm).

In vitro release (non-sink conditions) of exemplary formulation 6 (active ingredient dose 20 mg):

| | Time [min] | | | |
|---|---|---|---|---|
| | 15 | 30 | 60 | 90 |
| Release [%] | 79 | 82 | 83 | 83 |

(USP paddle, 75 rpm, 900 ml of acetate buffer of pH 4.5)

It is clear that exemplary formulation 6 displays a distinctly increased solubility (supersaturation) compared with micronized active ingredient (I) (comparison 1.1). A solubility which is higher by a factor of 2 is detectable after 1 hour.

Bioavailability

1) Comparative Study in Rats (3 mg/kg)

The bioavailability was investigated by administering 3 mg/kg active ingredient (I) in each case to male Wistar rats:
a) in the form of exemplary formulation 1 (suspended in water)
b) in the form of exemplary formulation 2 (suspended in water)
c) in the form of exemplary formulation 3 (suspended in water)
d) in the form of the micronized crystalline active ingredient in thermodynamically stable crystal modification I (suspended in 0.5% strength aqueous methylhydroxyethylcellulose (proprietary name: Tylose MH 300))

The corresponding pharmacokinetic parameters are listed in the table below (geometric means):

| | AUC (0-24) [mg · h/l] | AUC (0-24)$_{norm}$ [kg · h/l] | $C_{max}$ [mg/l] | $C_{max, norm}$ [kg/l] |
|---|---|---|---|---|
| Exemplary formulation 1 | 2.45 | 0.818 | 0.721 | 0.240 |
| Exemplary formulation 2 | 2.70 | 0.900 | 0.996 | 0.332 |
| Exemplary formulation 3 | 2.79 | 0.931 | 0.961 | 0.320 |
| Crystalline, micronized active ingredient | 0.762 | 0.254 | 0.222 | 0.074 |

Result:

Exemplary formulation 1 comprising active ingredient (I) in thermodynamically metastable crystal modification and exemplary formulations 2 and 3 comprising active ingredient (I) in amorphous form display a distinctly improved bioavailability compared with administration of the crystalline micronized active ingredient in the thermodynamically stable crystal modification I (factor of 3.2 for exemplary formulation 1; factor 3.5 for exemplary formulation 2 and factor of 3.7 for exemplary formulation 3).

2) Comparative Study in Dogs (150 mg/kg)

The bioavailability was investigated by crossover administration of 150 mg/kg active ingredient (I) in each case to 4 Beagle dogs:
e) in the form of exemplary formulation 1 (suspended in water)
f) in the form of the micronized crystalline active ingredient in crystal modification I (suspended in aqueous methylhydroxyethylcellulose (0.5%) (proprietary name: Tylose MH 300) with addition of 2% Solutol HS 15)

The corresponding pharmacokinetic parameters are listed in the table below (geometric means):

| | AUC (0-24) [mg · h/l] | AUC (0-24)$_{norm}$ [kg · h/l] | $C_{max}$ [mg/l] | $C_{max, norm}$ [kg/l] |
|---|---|---|---|---|
| Exemplary formulation 1 | 44.5 | 0.297 | 7.54 | 0.050 |
| Crystalline, micronized active ingredient | 12.2 | 0.081 | 2.22 | 0.015 |

Result:

Exemplary formulation 1 comprising active ingredient (I) in thermodynamically metastable crystal modification displays a distinctly improved bioavailability compared with administration of the crystalline micronized active ingredient in the thermodynamically stable crystal modification I (factor of 3.6).

3) Comparative Study in Dogs (20 mg per Dog Equivalent to about 2 mg/kg)

The bioavailability was investigated by crossover administration of 20 mg (that is about 2 mg/kg) active ingredient (I) in the form of the following tablet formulations in each case to 4 female Beagle dogs:

a) in the form of comparative formulation 1.2 (administration of in each case 2 tablets/dog)
b) in the form of exemplary formulation 4 (administration of in each case 2 tablets/dog)

The corresponding pharmacokinetic parameters are listed in the table below (geometric means):

|  | AUC (0-24) [mg · h/l] | AUC (0-24)$_{norm}$ [kg · h/l] | $C_{max}$ [mg/l] | $C_{max, norm}$ [kg/l] |
|---|---|---|---|---|
| Comparative formulation 1.2 | 1.84 | 0.938 | 0.447 | 0.228 |
| Exemplary formulation 4 | 2.71 | 1.39 | 0.665 | 0.341 |

Result:

Exemplary formulation 4 comprising active ingredient (I) in thermodynamically metastable crystal modification displays an improved bioavailability compared with comparative formulation 1.2 (tablet comprising crystalline micronized active ingredient (I) in the thermodynamically stable crystal modification I) (factor of about 1.5).

The invention claimed is:

1. Solid pharmaceutical dosage form which can be administered orally and has rapid release, the pharmaceutical dosage form comprising an active ingredient (I) that is 5-chloro-N-({(5S)-2-oxo-3-[4-(3-oxo-4-morpholinyl)phenyl]-1,3-oxazolidin-5-yl}methyl)-2-thiophenecarboxamide and an excipient, wherein the pharmaceutical dosage form
   (a) comprises the active ingredient (I) in amorphous form or thermodynamically metastable crystal modification, and
   (b) 80% of active ingredient (I) is released in a period of less than 2 hours in USP release method with apparatus 2 (paddle); and
   further wherein the active ingredient (I) is obtained in amorphous form by dissolving in a solvent
   or
   further wherein the active ingredient (I) is obtained in amorphous form or converted into a thermodynamically metastable crystal modification by melting
   or
   further wherein the active ingredient (I) is obtained in amorphous form or converted into a thermodynamically metastable crystal modification by melt extrusion.

2. Pharmaceutical dosage form according to claim 1, characterized in that 80% of active ingredient (I) is released in a period not exceeding 1 hour in USP release method with apparatus 2 (paddle).

3. Pharmaceutical dosage form according to claim 1, characterized in that the active ingredient (I) is obtained in amorphous form by dissolving in a solvent.

4. Pharmaceutical dosage form according to claim 3, wherein the active ingredient (I) is obtained in amorphous form by dissolving with one or more suitable excipients in acetic acid to form a resulting mixture, and the active ingredient (I) is present in a concentration of from 0.1 to 30% in the resulting mixture.

5. Pharmaceutical dosage form comprising granules comprising the active ingredient (I) according to claim 3.

6. Pharmaceutical dosage form according to claim 5 in the form of a capsule, of a sachet or of a tablet.

7. Process for producing a pharmaceutical dosage form according to claim 3, comprising dissolving the active ingredient (I) in a solvent, removing the solvent by distillation to produce a resulting mass, drying the resulting mass, grinding the dried mass, and (1) mixing the ground mass with the excipient and/or with further pharmaceutically suitable excipients and then packing the mixture as sachet or capsule or, (2) mixing with tabletting excipients, compressing to tablets, and coating the tablets.

8. Pharmaceutical dosage form according to claim 1, characterized in that the active ingredient (I) is amorphized or converted into a thermodynamically metastable crystal modification by melting.

9. Pharmaceutical dosage form according to claim 8, characterized in that one or more suitable excipients are employed in the melting, and the active ingredient (I) is present in a concentration of from 0.1 to 30% in the mixture resulting after the melting process.

10. Pharmaceutical dosage form according to claim 8 in the form of a capsule, of a sachet or of a tablet.

11. Process for producing a pharmaceutical dosage form according to claim 8, comprising preparing a mixture of the active ingredient (I) by melting, grinding the resulting mixture, and (1) mixing the ground mixture with the excipient and/or with further pharmaceutically suitable excipients and then packed as sachet or capsule or, (2) mixing the ground mixture with tabletting excipients, compressing to tablets, and coating the tablets.

12. Pharmaceutical dosage form according to claim 1, characterized in that the active ingredient (I) is amorphized or converted into a thermodynamically metastable crystal modification by melt extrusion.

13. Pharmaceutical dosage form according to claim 12, characterized in that hydroxypropylcellulose (HPC) or polyvinylpyrrolidone (PVP) is employed as polymer in the melt extrusion, the proportion of polymer in the melt extrudate is at least 40%, and the active ingredient (I) is present in the melt extrudate in a concentration of from 0.1 to 20%.

14. Pharmaceutical dosage form according to claim 12, characterized in that at least one pharmaceutically suitable substance is added in a concentration of from 0.2 to 40% as plasticizer for a polymer employed in the melt extrusion and/or for depressing the melting point of the active ingredient (I); wherein the pharmaceutically acceptable substance is selected from the group consisting of polyethylene glycol, polymethacrylates, polymethylmethacrylates, polyethylene oxide, polyoxyethylene-polypropylene block copolymers, vinylpyrrolidone-vinyl acetate copolymers, saturated polyglycolized glycerides and sugar alcohols.

15. Pharmaceutical dosage form according to claim 14, characterized in that the pharmaceutically suitable substance is a sugar alcohol.

16. Pharmaceutical dosage form according to claim 12 in the form of a capsule, of a sachet or of a tablet.

17. Process for producing a pharmaceutical dosage form according to claim 12, comprising producing an extrudate comprising the active ingredient (I) by melt extrusion, grinding the extrudate, and (1) mixing the ground extrudate with the excipient and/or with further pharmaceutically suitable excipients and then packing as sachet or capsule or, (2) mixing the ground extrudate with tabletting excipients, compressing to tablets, and coating the tablets.

18. Multiparticulate pharmaceutical dosage form according to claim 1.

19. Multiparticulate pharmaceutical dosage form according to claim 18, characterized in that the diameter of the particles is from 0.5 to 3.0 mm.

20. Pharmaceutical dosage form comprising multiparticulate pharmaceutical dosage forms according to claim 18.

21. Pharmaceutical dosage form according to claim 20 in the form of a capsule, of a sachet or of a tablet.

22. Process for producing the multiparticulate pharmaceutical dosage form of claim 18, comprising producing by melt extrusion an extrudate strand comprising the active ingredient (I) and cutting the extrudate strand.

23. Process according to claim 22, wherein the cutting of the extrudate strand results in shaped articles that are rounded.

24. Process according to claim 22, wherein shaped articles are formed by cutting the extrudate strand, the process further comprising coating the shaped articles.

25. Method for the treatment of a thromboembolic disorder selected from the group consisting of myocardial infarction, angina pectoris, reocclusions and restenoses following angioplasty or aortocoronary bypass, stroke, transient ischaemic attacks, peripheral arterial occlusive diseases, pulmonary embolisms and deep vein thromboses, the method comprising administering a therapeutically effective amount of the solid pharmaceutical dosage form of claim 1 to a patient in need thereof.

* * * * *

UNITED STATES PATENT AND TRADEMARK OFFICE
CERTIFICATE OF CORRECTION

PATENT NO. : 8,586,082 B2
APPLICATION NO. : 12/089148
DATED : November 19, 2013
INVENTOR(S) : Benke It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1501 days.

Signed and Sealed this
Twenty-sixth Day of May, 2015

Michelle K. Lee
*Director of the United States Patent and Trademark Office*